(12) United States Patent
Monfre et al.

(10) Patent No.: US 7,395,158 B2
(45) Date of Patent: Jul. 1, 2008

(54) METHOD OF SCREENING FOR DISORDERS OF GLUCOSE METABOLISM

(75) Inventors: Stephen L. Monfre, Gilbert, AZ (US); Linda Hockersmith, Tempe, AZ (US); Donald Hetzel, Key Largo, FL (US); Kevin H. Hazen, Gilbert, AZ (US); Andrew Cone, Victoria, MN (US)

(73) Assignee: Sensys Medical, Inc., Chandler, AZ (US)

( * ) Notice: Subject to any disclaimer, the term of this patent is extended or adjusted under 35 U.S.C. 154(b) by 0 days.

(21) Appl. No.: 10/219,200

(22) Filed: Aug. 13, 2002

(65) Prior Publication Data

US 2003/0054428 A1   Mar. 20, 2003

Related U.S. Application Data

(63) Continuation-in-part of application No. 09/766,427, filed on Jan. 18, 2001, now abandoned.

(60) Provisional application No. 60/312,155, filed on Aug. 13, 2001, provisional application No. 60/208,027, filed on May 30, 2000.

(51) Int. Cl.
*G06F 19/00* (2006.01)
*G01N 33/48* (2006.01)

(52) U.S. Cl. ............... 702/19; 702/23; 700/50; 700/52; 703/2; 422/68.1; 436/95; 600/316

(58) Field of Classification Search ............ 702/19, 702/21, 26, 32, 20; 703/2
See application file for complete search history.

(56) References Cited

U.S. PATENT DOCUMENTS

| | | | | |
|---|---|---|---|---|
| 5,750,345 | A * | 5/1998 | Bowie | 435/6 |
| 6,280,381 | B1 | 8/2001 | Malin | |
| 6,518,069 | B1 | 2/2003 | Otvos | |
| 6,853,854 | B1 | 2/2005 | Proniewicz | |
| 6,925,393 | B1 | 8/2005 | Kalatz | |
| 2002/0042143 | A1 | 4/2002 | Yatscoff et al. | |
| 2004/0197846 | A1 * | 10/2004 | Hockersmith et al. | 435/14 |

OTHER PUBLICATIONS

Graci et al., The intravenous insulin tolerance test is an accurate method for screening a general population for insulin resistance and related abnormalities. 1999, Journal of Endocrinological Investigation, vol. 22, pp. 472-475.*
"Tests and Procedures: Oral Glucose Tolerance Test (OGTT)", 2006, Cincinnati Children's Hospital Medical Center, on the world wide web at http://www.cincinnatichildrens.org/health/info/endocrine/tests, 2 pages.*

"Oral Glucose Tolerance Test (OGTT)", 2006, Diabetes Self-Management, R.A. Rapaport Publishing, Inc., on the world wide web at http://www.diabetesselfmanagement.com/article.cfm?aid=403 &sid=6, 2 pages.*
Al-Zurba, "Oral Glucose Tolerance Test (OGTT)", 2006, Diabetes and You, on the world wide web at http://www.sokkari.com/dx_oggt.htm, 2 pages.*
Albrecht, et al. Derwent accession No. 1990-084737, abstract for DD 8901404 (Jan. 14, 1990).
Steno Diabetes Center. Is fasting glucose sufficient to define diabetes? Epidemiological data from 20 European studies. Diabetologia. 1999, vol. 42, pp. 647-654, espicially pp. 648 and 650-651.
Leyva et al., "Factors of the Metabolic Syndrome," Arteriosclerosis Thrombotic Vascular Biology, 1998, vol. 18, pp. 208-214, especially p. 209.
Tamayo et al., "Interpreting patterns of gene expression with self-organizing maps," Proceedings of the National Academy of Sciences of the United States of America, Mar. 1999, Vo. 96, pp. 2907-2912, especially p. 2909.
Decode Study Group, "Is fasting glucose sufficient to define diabetes?" Epidemiological data from 20 European studies. Diabetologia 1999, vol. 42, pp. 647-654, especially No. 648.
Svanborg et al., "Associations between Plasma Glucose and DSM-II R Cluster B Personality Traits in Psychiatric Outpatients," Neuropsychobiology, 2000, vol. 41, pp. 79-87, especially Material and Methods.
Bonora et al., "Impaired Glucose Tolerance, Type II diabetes mellitus and carotid atherosclerosis: prospective results from Bruneck Study," Diabetologia, 2000, vol. 43, pp. 156-164, especially Material and Methods.
Young-Hyman et al., "Evaluation of the Insulin Resistance Syndrome in 5 to 10 year old Overweight/Obese African American Children," Diabetes Care, Aug. 2001, vol. 24, No. 8, pp. 1359-1364, especially p. 1360.
Feneberg et al., "Altered Temporal Organization of Plasma Insulin Oscillations in Chronic Renal Failure," The Journal of Clinical Endocrinology and Metabolism, May 2002, vol. 87, No. 5, pp. 1965-1973, especially Materials and Methods.

* cited by examiner

*Primary Examiner*—Carolyn Smith
(74) *Attorney, Agent, or Firm*—Michael A. Glenn; Glenn Patent Group

(57) ABSTRACT

A method of screening for disorders of glucose metabolism such as impaired glucose tolerance and diabetes allows prevention, or early detection and treatment of diabetic complications such as cardiovascular disease, retinopathy, and other disorders of the major organs and systems. A mathematical algorithm evaluates the shape of a subject's glucose profile and classifies the profile into one of several predefined clusters, each cluster corresponding either to a normal condition or one of several abnormal conditions. The series of blood glucose values making up the glucose tolerance curve may be measured using any glucose analyzer including: invasive, minimally invasive and noninvasive types. The method is executed on a processing device programmed to perform the steps of the method. Depending on the outcome of the screening, a subject may be provided with additional information concerning their condition and/or counseled to consult further with their health care provider.

24 Claims, 1 Drawing Sheet

METHOD OF SCREENING FOR DISORDERS OF GLUCOSE METABOLISM

CROSS-REFERENCE TO RELATED APPLICATION

This application is a continuation-in-part of U.S. patent application Ser. No. 09/766,427 filed Jan. 18, 2001, now abandoned which claims benefit of U.S. provisional patent application Ser. No. 60/208,027 filed May 30, 2000; and claims benefit of U.S. Provisional Patent Application Ser. No. 60/312,155, filed on Aug. 13, 2001.

BACKGROUND OF THE INVENTION

1. Field of the Invention

The invention relates generally to measurement of blood and tissue analytes. More particularly the invention relates to a method of screening for disorders of glucose metabolism.

2. Background Information

Diabetes is a chronic and incurable disease in which the body does not produce or properly use insulin, a hormone that allows glucose to enter the cells of the body and be utilized for energy. The cause of diabetes is not yet known, although both genetic and environmental factors such as obesity and lack of exercise appear to play roles. People with diabetes have increased risk of cardiovascular disease as well as retinopathy and neuropathy. It has been shown that tight control of glucose levels in the diabetic population to normoglycemic or slightly hyperglycemic levels results in delayed onset and slowed progression of retinopathy, nephropathy, and neuropathy [See DCCT study group, *The New England Journal of Medicine,* 341:1306:1309 (1993)].

With inadequate insulin utilization, glucose builds in the bloodstream instead of transporting into cells. The body is unable to use glucose for energy despite the increasing levels of glucose circulating in the blood. Initial glucose elevations may cause no symptoms. Later, the elevations may cause symptoms of fatigue, excessive thirst, urination, and hunger. These symptoms are non-descript and are often not reported to health care providers. Many people have unknown elevations for years without proper management of the disease because current diagnostic test procedures were either not ordered or not opportune during the health care visit.

There are three major types of diabetes:

Type I—Insulin Dependent Diabetes Mellitus (IDDM)—Also known as Juvenile-Onset Diabetes Type I diabetes is an autoimmune disease in which the body's own immune system destroys the pancreatic cells which produce insulin. This disease can occur at any age, but most often occurs in people under thirty years of age. Type I diabetes accounts for approximately ten percent of all diabetics. Presentation of symptoms is usually severe and develops rapidly. People with this condition require daily doses of insulin to stay alive. Although the exact cause of Type I diabetes is unknown, genetics, viruses that injure the pancreas, and destruction of insulin-making cells by the body's immune system may play causative roles.

Type II—Non-insulin Dependent Diabetes Mellitus (NIDDM)—Also known as Adult-Onset Diabetes Type II diabetes usually occurs due to a metabolic disorder known as insulin resistance, an inability to properly use insulin combined with relative insulin deficiency. This form of diabetes is the most common form of diabetes, accounting for approximately ninety percent of cases. People in the following categories are at a higher risk of developing Type II diabetes:

Over age forty-five;
Family history of diabetes;
Overweight;
Lack of regular exercise;
Low HDL cholesterol
High triglycerides;
Certain racial and ethnic groups; and
Women who have had gestational diabetes.

Gestational Diabetes

According to the American Diabetes Association, Gestational diabetes mellitus (GDM) is defined as glucose intolerance with onset or first recognition during pregnancy, whether or not the condition persists after pregnanoy. It does not exclude the possibility that unrecognized glucose intolerance may have antedated or begun concomitantly with the pregnancy.

Risk assessment for GDM should be undertaken at the first prenatal visit with testing undertaken at 24-28 weeks of gestation for those at high risk:

Age >25 years;
Overweight or obese;
Member of an ethnic group with a high prevalence of GDM;
Family history of diabetes;
History of stillbirth or high birth weight infants; or
Previous gestational diabetes.

Diabetes Prevalence and Trends

Approximately seven percent of all pregnancies are complicated by GDM, resulting in more than two hundred thousand cases annually. The prevalence may range from one to fourteen percent of all pregnancies, depending on the population studied and the diagnostic tests employed.

The World Health Organization estimates that diabetes currently afflicts one hundred fifty-four million people worldwide, fifty-four million of who live in developed countries. They also predict that the number of people with diabetes worldwide will grow to three hundred million by 2025.

As many as 15.7 million Americans, or 5.9% of the population, have diabetes with approximately 5.4 million of these people being undiagnosed. The number of Americans with diabetes has recently been estimated to be growing at a rate of nine percent per year.

In the United States, the prevalence of adults with diagnosed diabetes increased by six percent in 1999 and rose thirty-three percent nationally between 1990 and 1998. There are approximately eight hundred thousand new cases every year in America.

The risk for Type II diabetes increases with age. An estimated eighteen percent of the American population aged sixty-five and older has diabetes.

In addition to millions of Americans who suffer from diabetes, it is estimated that an additional twenty to thirty million Americans suffer from Impaired Glucose Tolerance (IGT). Approximately twenty-five percent of the American population aged sixty-five and older suffer from IGT.

Impaired Glucose Tolerence

It is estimated that eleven percent of the American public has this condition. Impaired glucose tolerance may be viewed as an intermediate condition between normal glucose metabolism and type II diabetes. Impaired glucose tolerance is a condition in which blood sugar levels are higher than normal, but do not meet the diagnostic criteria for diabetes.

Persons with IGT have a five-fold risk of developing diabetes within five years. However, the Diabetes Prevention Study has shown that early detection and intervention may delay or prevent the onset of diabetes. It also has recently been discovered that IGT individuals are at higher risk for cardiovascular disease and death, a risk evaluated in the Whitehall Study, the Paris Prospective Study, and the Helsinki Policeman Study [See *Diabetes Care,* 21:360-367 (1998)] and discovered to be greater than in people with diabetes. It is reasonable to suppose that with the early detection and treatment of IGT, strategies to mitigate cardiovascular risk as well as diabetes prevention may be pursued. Prevention or early treatment of diabetes would have the added benefit of reducing diabetic complications such as kidney disease, nerve disease, blindness, diabetic ketoacidosis, and a shorter lifespan. For these reason, early detection of IGT is critical to the general health of our population.

Hyperinsulinemia (Postprandial Reactive Hypoglycemia)

Postprandial reactive hypoglycemia is a medical condition in which symptoms occur after a meal as a response to food stimulation as opposed to a fasting state. Blood sugar levels are normally around 90 to 110 mg/dL, but with hypoglycemia they are usually below 50 mg/dL and may get as low as 35 mg/dL.

There are two reasons for the symptoms: 1) adrenaline release and 2) glucose deprivation of the nervous system. Low blood sugar stimulates the release of adrenaline, which causes shakiness, sweating, hunger pangs, nervousness, and irritability. The brain doesn't get enough sugar, and commonly reported symptoms are headache, mental dullness, and fatigue. If the blood sugar drops too low, a person can get confused, have visual problems, develop a seizure, or even become unconscious.

It is theorized that the cause of the abnormal response stems from first phase vs. second phase insulin release mechanisms in the pancreas. First phase release is diminished allowing a rapid increase in blood glucose levels. It is followed by an over-responsive second phase release causing a dramatic drop in glucose to hypoglycemic levels. Some people with reactive hypoglycemia go on to develop diabetes.

Adverse Clinical Effects of Diabetes and Impaired Glucose Tolerence

Diabetes and impaired glucose tolerance have been called "silent killers" because many people are unaware that they have the disease until they develop one of its life-threatening complications. Complications of diabetes include retinopathy, neuropathy, and cardiovascular problems.

Heart Disease and Stroke: People with diabetes are two to four times more likely to have heart disease or suffer a stroke. Additionally, heart disease is present in seventy-five percent of diabetes-related deaths.

Kidney Disease: Long-term hyperglycemia results in the kidneys filtering excess blood. This extra work results in small leaks. Protein is lost into the urine. A small amount of protein in the urine is microalbuminuria while a larger concentration is proteinuria or macroalbuminuria. The overwork also diminishes the filtering capacity of the kidneys, ultimately leading to end-stage renal disease. While not everyone who has diabetes develops kidney disease, diabetes is the leading cause of end-stage renal disease, accounting for about forty percent of new cases each year. Between ten and twenty percent of all diabetics develop kidney disease due to diabetic nephropathy and require dialysis or a kidney transplant in order to stay alive.

Neuropathy (Nerve Disease and Amputations): A common complication of diabetes is diabetic neuropathy, which is a group of nerve diseases affecting peripheral nerves especially those of the fingertips and toes. Roughly two-thirds of diabetics have some form of neuropathy with symptoms ranging from loss of sensation in the feet to lower limb amputation due to unnoticed infections. Each year, fifty-six thousand Americans lose a lower limb to diabetes.

Retinopathy: Retinopathy includes all abnormalities of the small blood vessels of the retina caused by diabetes. Most diabetics have nothing more than minor eye disorders related to their diabetes. However, diabetes is the leading cause of new cases of blindness among those aged twenty to seventy-four years with twelve thousand to twenty-four thousand new blindness cases due to diabetic retinopathy occurring each year. Overall, people with diabetes have a higher risk of blindness. Early detection and treatment of diabetes can reduce the risk of blindness in many patients.

Diabetic Ketoacidosis (DKA): One of the most serious outcomes of poorly controlled diabetes, DKA is marked by high blood glucose levels along with ketones in the urine and occurs primarily in Type I individuals. DKA is responsible for about ten percent of diabetes-related deaths in individuals under age forty-five.

Skin Conditions: Diabetes may also affect the skin. Up to one third of diabetics may have a skin disorder during some part of their life. Skin problems that occur primarily with diabetics are dermopathy, necrobiosis lipoidica diabeticorum, diabetic blisters, and eruptive xanthomatosis.

Gum Disease: There is an increased risk in diabetics of developing periodontal disease. Excess circulatory glucose contributes to bacterial plaque formation.

Shorter Lifespan: Life expectancy of people with diabetes averages fifteen years less than people without the disease. Diabetes is the seventh leading cause of death in the United States, contributing to approximately two hundred thousand deaths per year.

Impotence: Males are more likely to experience impotence due to changes or disturbances in the peripheral nervous system (neuropathy) or blood vessel blockage. Impotence affects approximately thirteen percent of men with Type I diabetes and eight percent of men with Type II diabetes.

Fetal Complications: Infants of gestationally diabetic mothers are at higher risk of fetal anomalies, e.g. birth defects, macrosomia, higher birth weights, post-partum hypoglycemia, and respiratory distress syndrome.

In view of the above, there exists a great need in the art for a rapid, convenient, and economical method for routine and early detection of disorders of glucose metabolism.

SUMMARY OF THE INVENTION

The invention provides a method of screening for disorders of glucose metabolism such as impaired glucose tolerance and diabetes, thereby allowing early treatment of the condition and possibly enabling prevention, or early detection and treatment of common complications such as cardiovascular disease, retinopathy, and other disorders of the major organs and systems. A mathematical algorithm evaluates the shape of a subject's blood glucose profile before and after a glucose challenge and classifies the profile into one of several predefined clusters, each cluster corresponding either to a normal condition or one of several abnormal conditions. Evaluation of the shape of the profile is accomplished through examination of one or more parameters of the profile. One embodiment of the invention provides a simple algorithm that directly compares parameters to established thresholds and ranges for the various conditions. A further embodiment of the invention provides a fuzzy algorithm that computes a screening factor by calculating a weighted average of the parameters. The screening factor is then compared with thresholds determined from common diagnostic criteria. Preferably, the time series of blood glucose concentrations making up the glucose tolerance curve is measured using a noninvasive glucose analyzer, however any type of glucose analyzer, including minimally invasive and invasive devices, is suitable for practice of the invention. The values need not be actual values, relative values are also suitable, because the invention evaluates the shape of the profile, which can be discerned based on relative values. Additionally, the fuzzy algorithm can evaluate the profile even if parameters are missing. In addition, missing data can be supplied from historical data.

The evaluation and classification is accomplished by a processing device specifically programmed to perform the method's steps. Depending on the outcome of the screening, a subject may be provided with additional information concerning their condition and/or counseled to consult further with their health care provider.

DETAILED DESCRIPTION

Figure 1:
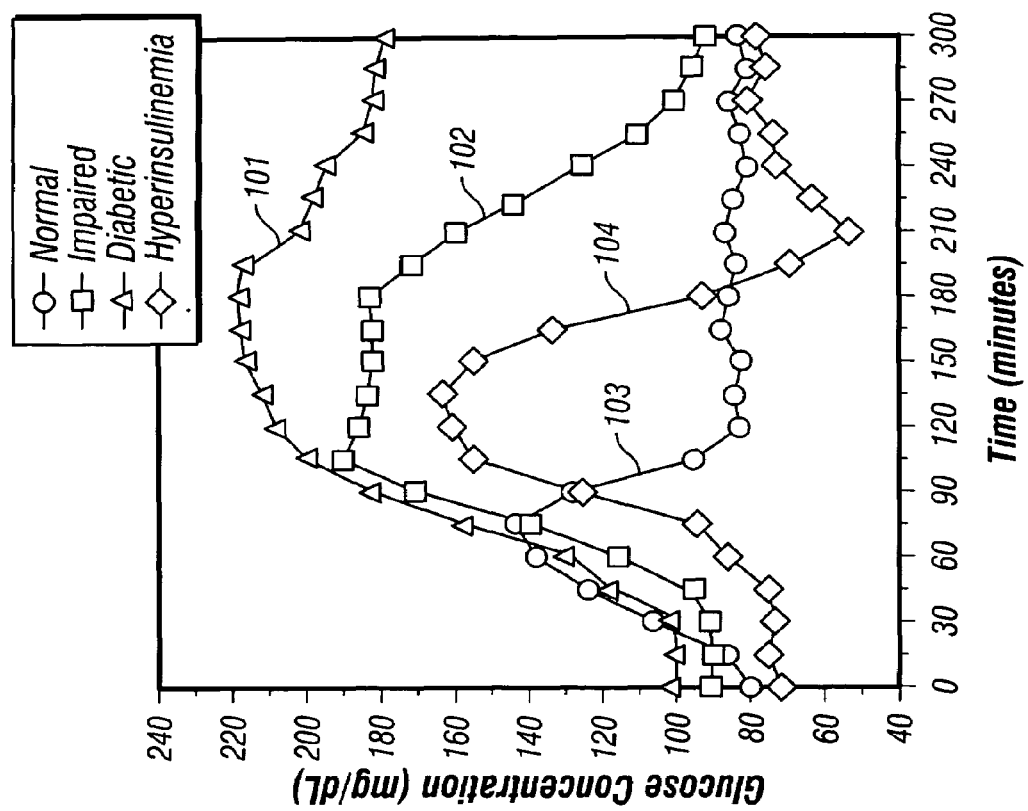
FIG. 1 shows blood glucose concentration curves for normal glucose tolerance, impaired glucose tolerance, diabetes, and hyperinsulinemia.

Glucose tolerance tests are well known and may be used to test a variety of disorders of glucose metabolism and hormone secretory disorders. Basically, glucose is ingested in the form of a high glucose concentration beverage or as a carbohydrate rich food. Glucose concentrations are then monitored periodically (often every hour) for a period of 3-5 hours, depending upon the suspected diagnostic endpoint. The shape of the glucose profile of the resulting data set may then be utilized to further identify the medical condition. For example, diabetes is diagnosed based upon the overall increase in glucose concentration from the initial fasting condition and the amount of time required for the glucose concentration to drop to a normal physiological glucose concentration of 80-120 mg/dL. In this invention, the glucose response profile shape as a function of time relative to a glucose challenge is utilized as input data to an algorithm that evaluates the profile and then classifies the profile that outputs a screening response indicating that the subject being tested either has diabetes, IGT (impaired glucose tolerance), a normal physiological response, or abnormally low glucose tolerance (LGT). The input values may be those of blood glucose determinations collected once every ten to thirty minutes. In keeping with the object of providing a convenient, inexpensive screening method, it is preferable that the glucose measurements be made with a non-invasive analyzer, however minimally invasive and invasive devices are entirely suitable for practice of the invention. FIG. 1 shows representative glucose concentration profiles for a diabetic 101, a subject with IGT 102, a subject with a normal physiological glucose response 103, and a low glucose response 104 as a function of time. The algorithm is executed on processing device appropriately programmed using conventional computer programming techniques.

The typical diabetic profile shape 101 is often observed to start off at a higher fasting glucose concentration, rise to higher concentrations (typically above 180 mg/dL) often at a faster rate, maintain higher glucose concentrations for a longer period of time, and take longer to return towards a normal physiological glucose concentration of 80 to 120 mg/dL. After the peak, the rate of decrease of the glucose concentration may be minimal versus a subject with IGT or with normal physiological glucose response.

The IGT profile shape 102 has a response that starts with normal fasting glucose levels, rises quickly to levels between 140-200 mg/dL, and then falls back to normal. However, the return to normal glucose concentration typically occurs with a slower negative rate of change compared to a normal physiological response.

A normal glucose response profile 103 has a shape that shows a slight increase in glucose levels to <140 mg/dL and generally returns within two hours to normal levels. The shape may be quite angular with very quick rates of glucose change indicating normal insulin function. The final segment of the profile is generally flat in the normal ranges.

Low glucose tolerance 104 (LGT) or hyperinsulinemia produces a shape or profile that starts with low to normal fasting glucose levels. The shape then shows a sharp increase in glucose response. The peak of the shape is usually dramatic, as glucose levels rarely linger in the elevated range. A shape with a peak at two hours might be indicative of a different phase two insulin response than that of a peak at three to four hours. The decrease continues through the normal range to blood glucose levels typically below 60 mg/dL. Hypoglycemia triggers the adrenergic response causing the shape of the response to rise again into normal ranges.

In a first embodiment of the invention, a simple comparison algorithm is provided that compares selected parameters from a subject's profile with predetermined thresholds for the various conditions. The thresholds may be determined from standard diagnostic criteria for the various conditions. For example, a diabetic has a fasting plasma glucose level greater than or equal to 140 mg/dL or a 2-hour post challenge glucose level greater than or equal to 200 mg/dL. A subject with impaired glucose tolerance has a fasting plasma glucose level less than 126 mg/dL and/or a 2-hour post challenge glucose level between 140 mg/dL and 200 mg/dL. A person with normal physiological tolerance has a fasting plasma glucose concentration of less than 140 mg/dL and/or a two-hour post challenge glucose concentration less than 140 mg/dL. An individual suffering from LGT typically has a fasting plasma glucose level less than 85 mg/dL and/or a 2-hour post challenge glucose level between 140 mg/dL and 200 mg/dL, and a 3-4 hour post challenge glucose level less than 70 mg/dL. The algorithm compares the values of the subject's profile with the predetermined thresholds, and on the basis of the comparison classifies the profile (and thus, the subject) as normal, diabetic, having IGT, or having LGT. The above parameters are exemplary only. One skilled in the art will appreciate other parameters and combinations that are consistent with the spirit and scope of the invention.

Once a classification has been made (diabetic, IGT, normal, LGT), information about related diabetic diseases/symptoms may be presented to the subject. For example, if a subject is classified as having impaired glucose tolerance, then the subject would be made aware that they are at risk for heart disease, stroke, kidney disease, neuropathy, retinopathy, diabetic ketoacidosis, skin conditions, gum disease, impotence, and/or a shorter lifespan. The subject may be counseled to seek the advice of their healthcare practitioner.

In an alternate embodiment, glucose concentration values as a function of time are input to a fuzzy mathematical algorithm that evaluates the series to determine if the range of values screens the subject as a diabetic, as having IGT, normal physiological function, or LGT. A number of parameters may be utilized individually or in combination to make this determination. These parameters are identified in FIG. 2.

Figure 2:
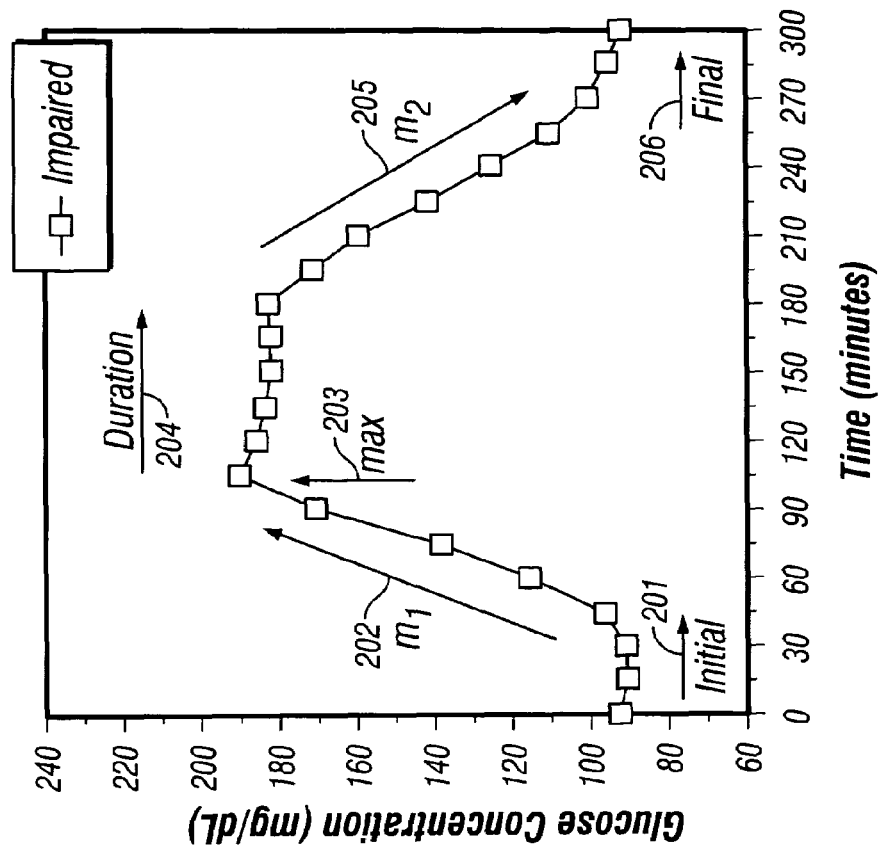
FIG. 2 indicates a variety of parameters on a blood glucose profile that are used to evaluate the profile according to the invention.

The first parameter 201 is the initial glucose concentration (FIG. 2: Initial). An increased initial glucose concentration is diagnostic of diabetes. The ADA (American Diabetes Association) states that an initial fasting glucose concentration of greater than 126 mg/dL is an indication of diabetes. The ADA also states, in the absence of external insulin injections, a fasting glucose concentration less than 123 mg/dL is indicative of normal physiological function but could also be IGT. However, in this fuzzy algorithm more extreme numbers are assigned to a diabetic and normal state so that a range of weights from 0 to 1 can be assigned to intermediate levels. For example, a fasting glucose concentration >140 mg/dL is a very strong indication of diabetes and could be assigned a value of 1, as are all fasting glucose concentrations above 140 mg/dL. A fasting glucose concentration of 80 mg/dL is an indication of normal physiological function and could be assigned a value of 0, as are all glucose concentrations less than 80 mg/dL. A linear or nonlinear scale can then be applied between the two values. Thus, on a linear scale, a glucose concentration of 120 is assigned a weight of 0.66. This indicates a reasonable likelihood of IGT whereas a weight of 1 is indicative of diabetes and a weight of 0 is indicative of normal physiological function.

For LGT screening, a fasting glucose concentration less than 50 mg/dL is an indication of LGT and would be assigned a value of 0. A linear or non-linear scale can then be applied between the values of <50 mg/dL and 80 mg/dL. With a linear scale, a value of 65 mg/dL would be assigned a value of 0.55. Prior to an evaluation of LGT, additional parameters would be necessary. Alternately, a single scale can be employed to diagnose all conditions. In this case, a fasting glucose concentration of 50 mg/dL, indicative of LGT has a weight of 0, a normal blood glucose concentration of 80 mg/dL has a weight of 0.33 and the diabetic value of 140 mg/dL still has a weight of 1.

A second parameter 202 is the rate at which the glucose concentration rises (FIG. 2: $m_1$). In general, a higher slope is indicative of diabetes while smaller slopes indicate IGT and still smaller slopes are indicative of a normal physiological response. Initial slopes indicative of diabetes may range from 1 to 7 mg/dL/min; whereas, normal physiological function results in rates of change from 0 to 2 mg/dL/min. Intermediate rates are indicative of IGT. Due to the fact that the rates from each cluster overlap, only more extreme values could lead to an accurate classification, based on evaluation of the rate of change. As described above, high slopes (above 3 mg/dL/min) may be assigned a weight of 1 while low slopes (less than 0.5 mg/dL/min) may be assigned a value of zero. Again using a linear scale, a slope of 2.5 mg/dL/min would be assigned a weight of 0.8 and would be interpreted as a positive screening for diabetes.

A third parameter 203 is the maximum monitored glucose concentration (FIG. 2: max). Glucose levels peaking above 220 mg/dL are an indication of diabetes, and may be assigned a weight of 1. Only a slight rise above the high end of the normal glucose concentration of 120 mg/dL is indicative of normal physiological activity. Thus, glucose concentrations of 120 mg/dL or below may be assigned a weight of 0. Elevated but not grossly high glucose concentrations (160 to 220 mg/dL) are indicative of IGT and are then assigned intermediate weights. A positive correlation is known to exist between the diagnosis of normal, IGT, or diabetes with the peak glucose concentration monitored. This correlation is well known and accepted; therefore, this parameter may be given a larger weighting function.

A fourth parameter 204 is the duration that the glucose concentration remains elevated (FIG. 2: duration). The longer the duration above a given threshold, the more indicative the data are of diabetes. For example, 15 minutes above 200 mg/dL may indicate IGT while 1 hour above 200 mg/dL is indicative of diabetes.

A fifth parameter 205 is the rate of decrease of the glucose concentration after the peak glucose concentration (FIG. 2: $m_2$). Typically, the sharper the decrease, the more on the continuum the data is toward normal physiological function. As observed in FIG. 1, there exists a decent spread of rate of changes after the peak glucose concentration for subjects ranging from diabetic to normal, making this parameter a particularly sensitive indicator for diabetes or for IGT. Thus, this parameter may be then be given a larger weighting function.

A sixth parameter 206 is the minimum glucose concentration obtained after the maximum (FIG. 2: final). Glucose values that fall below 120 mg/dL without a dose of insulin are indicative of normal physiological response whereas glucose concentrations that stay above 150 mg/dL are indicative of diabetes. Glucose values that fall below 80 mg/dL could be indicative of LGT. As with the first parameter, values below 50 mg/dL would be assigned a value of 0 and at 150 mg/dL a value of 1.

One or more of these parameters may be utilized to determine if the subject is diabetic, has impaired glucose tolerance, has a normal physiological response, or low glucose tolerance according to equation 1, where SF is the screening factor, $P_{(1-6)}$ are parameters, and $W_{(1-6)}$ are weights:

$$SF = \frac{(P_1 W_1 + P_2 W_2 + P_3 W_3 + P_4 W_4 + P_5 W_5 + P_6 W_6)}{(W_1 + W_2 + W_3 + W_4 + W_5 + W_6)} \quad (1)$$

One or more of the parameters may be utilized to compute the screening factor and weights for each parameter may range from 0 to 1. Essentially, the screening factor is a weighted average of the individual scaled parameters. An average or a weighted final score can be computed from the individual score(s). Thresholds can then be determined to classify the subject into one of the three clusters. Any number of limits defining diabetic or non-diabetic may be established. Similarly linear or nonlinear axes may be established for any of the scores. These parameters may be established based on the most current diagnostic criteria provided by bodies such as, for example, the American Diabetes Association.

An example of a possible threshold screen limit would be:

$$SF_1 = \frac{(P_1 W_1 + P_6 W_6)}{(W_1 + W_6)}; \text{ and}$$

$$SF_2 = \frac{(P_2 W_2 + P_3 W_3 + P_4 W_4 + P_5 W_5)}{(W_2 + W_3 + W_4 + W_5)};$$

where:
$SF_1 < 0.25$ and $SF_2 < 0.1$ indicates normal glucose tolerance;
$0.25 < SF_1 < 0.5$ and $0.1 < SF_2 < 0.16$ indicates LGT;
$0.5 < SF_1 < 0.75$ and $0.16 < SF_2 < 0.325$ indicates IGT; and
$SF_1 > 0.75$ and $SF_2 > 0.325$ indicates diabetes.

Any additional combination would indicate the likelihood of a medical condition related to insulin and glucose tolerance exists, but is not readily defined in the individual's current physiological state. Such a screening outcome suggests that the individual's primary care physician performs addition tests.

Other algorithms for providing the same information will occur to those skilled in the art and all are entirely within the scope of the invention. As the understanding of diabetes and diabetes screening increases, it is expected that the criteria set forth by the ADA and WHO will change, thus making it necessary to adjust the threshold values to meet current diagnostic criteria.

It is noted here that a complete glucose profile is not required for this approach to function. Missing data points can be overcome, as the data points are not independent from one another. Thus, some of the data from each parameter can be absent. In fact, if all of the data from some parameters is absent the algorithm may still function by setting the weighting function for that parameter to zero. Inasmuch as glucose profiles tend to reproduce from day to day, partial data from each day may be utilized in the function. While this will decrease the precision of the screening factor, it allows historical data to be utilized in place of a glucose or meal tolerance test. This would minimize the pain involved with invasive or minimally invasive glucose testing. In some instances, such as when a subject has good record keeping of meal, glucose concentrations and/or insulin dosages, this data could be utilized as the input data minimizing data collection time.

Importantly, actual glucose concentrations are not required if relative glucose concentrations are available. As it is the shape of the response that is utilized in the screening, differences in glucose concentration can be utilized to obtain a screening factor. For example, if a noninvasive or minimally invasive glucose testing procedure shows a relative increase in glucose concentration between the fasting level and the maximum concentration, then parameters 1 (fasting) and 3 (maximum) may be utilized to determine the screening factor without actual glucose concentrations.

Subjects may be screened in an obstetric setting for relative change in glucose concentration as an early screen for gestational diabetes. Actual numbers would not be required as the response or shape could easily be identified as impaired. Some clinicians may choose to initiate early interventions such as diet and self-blood glucose monitoring based upon the detection of the impairment. Additional time to schedule diagnostic procedures may be precious because the pregnancy may already be at a relatively advanced stage.

In high-risk settings, for example, HIV or pulmonary clinics could use this bloodless approach to screen patients who might develop glucose abnormalities as a response to certain drug treatment therapies. The work place setting could use routine employee screenings for either glucose impairment or relative risk of complications.

Within a glucose profile, the individual data points are not independent. This allows outliers to be determined. Utilizing an individual glucose reading, only gross outliers may be detected. For example, a glucose reading of 20 with a conscious subject would be determined to be an outlier. However, with multiple data points, small outliers may be determined. For example, if every 20 minutes the glucose readings are 80, 100, 120, 140, 160, 180, 142, 220, 240 mg/dL then the data point 142 is an outlier. Using a traditional two point test at fasting and at 2 hours, the 80 mg/dL would be the fasting and the 142 mg/dL would be the 2-hour point. This person would be screened as having a normal physiological glucose response due to the outlier when in fact they are diabetic. Hence, the algorithm has built in safeguards against some poor screening hazards.

The screening algorithm of equation 1 allows early detection of IGT. Complications associated with diabetes may thus be discovered earlier. Early treatment can then be initiated. Being made aware of the condition which is largely due to environmental factors and to parameters such as body fat will allow the individual to mitigate or prevent future diabetes related complications.

Additional Embodiment:

The above embodiments have dealt with the obtaining actual values of blood glucose. Screening can also be done based on relative blood glucose values. Parameter 1 would be dropped (i.e. standardized to a given value, say 100 mg/dL), while Parameter 3 would be adjusted to focus on the range of blood glucose values, rather than the maximum. Generally, individuals having normal glucose tolerances will not experience a change greater than 60 mg/dL, while someone suffering from IGT or LGT will see a change greater than 60 mg/dL, but unlikely to experience a change greater than 100 mg/dL. People suffering from diabetes often experience changes greater than 100 mg/dL. Thus the fuzzy logic would apply a weighting factor of 0 to range values <60 mg/dL and a weighting factor of 1 to range values greater than 100 mg/dL.

Parameter 6 would then need to be modified to account for LGT. This would be achieved by assigning a weighting factor of 0 to range values >−30 mg/dL from the standardized value and a weighting factor of 2 to a range values >30 mg/dL from the standardized value at the 3-4 hour mark of the tolerance test.

The invention finds application in healthcare facilities including, but not limited to: physician offices, hospitals, clinics, and long-term healthcare facilities. Alternatively, this technology could be utilized in public settings such as shopping malls and the workplace, or in private settings such as the subject's home.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method of screening a subject for disorders of glucose metabolism, comprising the steps of:
    obtaining at least a portion of a glucose concentration profile for the subject using:
    a noninvasive blood glucose concentration analyzer, said profile comprising a plurality of blood glucose values after ingestion of food and said profile being obtained within five hours of said ingestion of food;
    evaluating shape of said profile using one or more parameters of said shape; and
    classifying said subject into at least one predetermined cluster using evaluation of said shape,
    wherein said cluster comprises at least one of
        diabetes;
        impaired glucose tolerance;
        normal physiological response; and
        low glucose tolerance;
    wherein classifying said subject provides information concerning said subject's condition to said subject and/or a practitioner.

2. The method of claim 1, wherein said plurality of blood glucose values comprises a time series.

3. The method of claim 1, wherein said blood glucose values are actual values.

4. The method of claim 1, wherein said blood glucose values are relative values.

5. The method of claim 1, wherein said parameters include any of:
   initial fasting glucose concentration; and
   glucose concentration after elapse of a predetermined time interval.

6. The method of claim 5, wherein said evaluating step comprises:
   comparing any of said parameters with predetermined values and/or ranges of values for each parameter indicative of either a normal condition or one of a plurality of abnormal conditions.

7. The method of claim 6, wherein each of said at least one predetermined clusters corresponds to one of said normal and abnormal conditions, said normal and abnormal conditions comprising:
   normal;
   impaired glucose tolerance;
   diabetic; and
   low glucose tolerance.

8. A method of screening a subject for disorders of glucose metabolism, comprising the steps of:
   obtaining at least a portion of a glucose concentration profile using any of:
      a noninvasive blood glucose concentration analyzer;
      a minimally invasive blood glucose concentration analyzer; and
      an invasive blood glucose concentration analyzer,
   said profile comprising a plurality of blood glucose values after ingestion of food and said profile being obtained within five hours of said ingestion of food;
   evaluating shape of said profile using one or more parameters of said shape; and
   classifying said subject into at least one predetermined cluster using evaluation of said shape;
   wherein classifying said subject provides information concerning said subject's condition to said subject and/or a practitioner,
   wherein said evaluation step comprises: determining a weight for each of said parameters using a fuzzy algorithm.

9. The method of claim 8, wherein said step of determining a weight comprises the step of:
   assigning each parameter a value on either a linear or non-linear scale, wherein said assigned value comprises said weight.

10. The method of claim 9, wherein minimum and maximum of said scale correspond to predetermined threshold values for a normal condition and a diabetic condition, respectively.

11. The method of claim 9, wherein minimum and maximum of said scale correspond to predetermined threshold values for a low glucose tolerance and a normal condition, respectively.

12. The method of claim 9, wherein minimum and maximum of said scale correspond to predetermined threshold values for a low glucose tolerance and a diabetic condition, respectively.

13. The method of claim 9, wherein ranges of values represented by said scale are established according to standard diagnostic criteria.

14. The method of claim 9, wherein missing parameters are assigned a weight of zero.

15. The method of claim 9, wherein missing data are supplied from historical data.

16. The method of claim 9, further comprising the step of calculating one or more screening factors based on actual or relative values of said parameters and said weights.

17. The method of claim 16, wherein said step of calculating screening factors comprises the step of calculating a weighted average of said weighted parameters according to:

$$SF = \frac{(P_1W_1 + P_2W_2 + P_3W_3 + P_4W_4 + P_5W_5 + P_6W_6)}{(W_1 + W_2 + W_3 + W_4 + W_5 + W_6)}$$

wherein SF=said screening factor and $P_1$=a first parameter, said first parameter comprising glucose concentration, $P_2$=a second parameter, said second parameter comprising rate at which glucose concentration rises, $P_3$=a third parameter, said third parameter comprising maximum monitored glucose concentration; $P_4$=a fourth parameter, said fourth parameter comprising duration that glucose remains elevated; $P_5$=a fifth parameter, said fifth parameter comprising rate of decrease of glucose concentration after a peak; and $P_6$=a sixth parameter, said sixth parameter comprising minimum glucose concentration after a maximum; and
wherein $W_1$=a weighting factor.

18. The method of claim 16, wherein said step of calculating screening factors comprises the steps of:
   calculating a weighted average of a first set of selected weighted parameters using the equation:

$$SF_1 = \frac{(P_1W_1 + P_6W_6)}{(W_1 + W_6)}$$

wherein $SF_1$=a first screening factor; and
   calculating a weighted average of a second set of selected weighted parameters using the equation:

$$SF_2 = \frac{(P_2W_2 + P_3W_3 + P_4W_4 + P_5W_5)}{(W_2 + W_3 + W_4 + W_5)}$$

wherein $SF_2$=a second screening factor, and $P_1$=a first parameter, said first parameter comprising glucose concentration; $P_2$=a second parameter, said second parameter comprising rate at which glucose concentration rises; $P_3$=a third parameter, said third parameter comprising maximum monitored glucose concentration; $P_4$=a fourth parameter, said fourth parameter comprising duration that glucose remains elevated; $P_5$=a fifth parameter, said fifth parameter comprising rate of decrease of glucose concentration after a peak; and $P_6$=a sixth parameter, said sixth parameter comprising minimum glucose concentration after a maximum; and
   wherein $W_1$=a weighting factor.

19. The method of claim 16, further comprising the step of establishing threshold screening limits using said screening factors.

20. The method of claim 1, wherein said parameters include any of:
initial fasting glucose concentration;
   rate of increase of glucose concentration following said glucose challenge;
   peak monitored glucose concentration;
   duration glucose remains elevated;
   rate of decrease of glucose concentration following said peak concentration; and
   minimum glucose concentration following said peak concentration.

21. The method of claim 1, further comprising the step of advising said subject of screening results.

22. The method of claim 1, further comprising the step of advising said subject of health risks from complications resulting from subject's condition.

23. The method of claim 1, wherein a processing device so programmed executes said steps.

24. The method of claim 1, wherein said food comprises any of a glucose beverage and a carbohydrate-rich food.

* * * * *